United States Patent [19]

Masson et al.

[11] 4,279,617

[45] Jul. 21, 1981

[54] IUMMUNOASSAY INVOLVING AGGLUTINATION

[75] Inventors: Pierre L. Masson, Brussels; Cesar L. Cambiaso, Kraainem, both of Belgium; Floris De Steenwinkel, Leidschendam, Netherlands; Adrian E. Leek, Bucks, United Kingdom

[73] Assignee: Technicon Instruments Corporation, Tarrytown, N.Y.

[21] Appl. No.: 124,849

[22] Filed: Feb. 26, 1980

[30] Foreign Application Priority Data

Feb. 26, 1979 [GB] United Kingdom ............... 06686/79

[51] Int. Cl.³ .................... G01N 33/54; G01N 33/56; G01N 33/58
[52] U.S. Cl. .............................. 23/230 B; 23/230 A; 23/915; 252/408; 422/57; 424/1; 424/8; 424/12; 435/7
[58] Field of Search ......................... 23/230 B; 424/12

[56] References Cited

U.S. PATENT DOCUMENTS

| | | | |
|---|---|---|---|
| 4,092,114 | 5/1978 | Buck | 23/230 B |
| 4,102,990 | 5/1978 | Uzgiris | 23/230 B X |
| 4,138,213 | 2/1979 | Masson | 23/230 B |
| 4,141,965 | 2/1979 | Soothill | 23/230 B X |
| 4,162,895 | 7/1979 | Cambiaso | 23/230 B X |
| 4,169,138 | 9/1979 | Jonsson | 23/230 B X |
| 4,185,084 | 1/1980 | Mochida | 23/230 B X |
| 4,189,466 | 2/1980 | Ainis | 23/230 B X |
| 4,210,622 | 7/1980 | Soothill | 23/230 B X |

*Primary Examiner*—Sidney Marantz
*Attorney, Agent, or Firm*—S. P. Tedesco

[57] ABSTRACT

A particle agglutination assay for antigens, antibodies and other binding proteins such as rheumatoid factor, uses two different, microscopic or submicroscopic particulate reagents. The first particulate reagent binds with the antigen or antibody under assay, and then the second particulate reagent is added which binds only to those first reagent particles which have bound to the antigen or antibody under assay, so causing agglutination. The free unbound first or second particles are assayed to indicate the presence and/or amount of the antigen or antibody under assay. The assay of rheumatoid factor may be so conducted to reveal the fractions of each immunoglobulin class of RF present. The assay is particularly useful for small quantities of antibodies present in human sera indicating allergy, infection or autoimmune diseases.

15 Claims, No Drawings

IUMMUNOASSAY INVOLVING AGGLUTINATION

This invention relates to the analysis of liquids, particularly but not exclusively biological fluids such as serum, for the presence therein of immunochemical substances such as antigens or antibodies. In this specification, the symbols "Ag", "Ab" and "Ab:Ag" are used, respectively, for antigen(s) (by which term we include haptens and other substances which can be bound by antibodies or similar binding proteins), antibody(ies) (including similar binding proteins and proteins such as rhematoid factor (RF), C1q, the active constituent of mouse serum and of mouse ascitic fluid) and complexes formed between Ag and Ab.

It is well known that Ag will react with an appropriate Ab to form Ab:Ag and most immunoassay procedures make use of this reaction. It is further known to coat particulate materials such as polystyrene (generally referred to as latex) with an Ab or Ag, and then to expose the coated particles to a sample solution under test, to see whether and to what extent the particles become agglutinated. Agglutination indicates the presence in the sample of an Ab or Ag capable of reacting with two or more coated latex particles to cause agglutination.

Whilst the technique of observing agglutination of coated particles is in many respects satisfactory, there are problems in assaying small quantities (in particular low concentrations) of Ab or Ag. The small quantity of Ab or Ag can be insufficient to provide a reliably observable agglutination of the Ag- or Ab-coated latex, respectively. Thus, owing to the size and hence mass differences between either antigens or antibodies and normally used latex particles, detectable agglutination only occurs when several antigen/antibody bridges are formed between two or more latex particles. If, however, the number of antigen or antibody molecules is very small, the statistical probability that several antibody bridges can be formed for each agglutination is very low and hence agglutination is also very small.

We have now found a way of overcoming this problem by using two different coated particles. According to the invention, the Ab or Ag to be assayed is mixed with a first particulate reagent which binds with the Ab or Ag. The binding reaction is reversible and may be illustrated as:

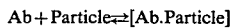

$$Ab + Particle \rightleftharpoons [Ab.Particle] \qquad (1).$$

The small amount of agglutination which occurs will be insufficient to allow accurate and reliable measurement. To the mixture, there is then added in excess a second particulate reagent. This second reagent binds with the (Ab.Particle) complex to form an agglutinate, thus effectively removing the complex from the equilibrium which is then displaced to the right (equation (1)). Substantially all the Ab or Ag under assay may then be converted to complex and then to agglutinate. By measuring the amount of first reagent or second reagent remaining unagglutinated in the mixture, the presence and/or amount of the Ab or Ag can be determined.

According to the present invention, therefore, there is provided a method of testing a liquid for a specific Ab or Ag therein, which comprises:

(a) mixing the liquid with a first microscopic or sub-microscopic particulate reagent which binds with the particular Ab or Ag under assay to form a complex therewith;

(b) adding to the mixture from step (a) a second microscopic or sub-microscopic particulate reagent which binds with the complex formed in step (a) to form an agglutinate, but does not bind with free first particulate reagent; and (c) selectively assaying the unagglutinated first or second particulate reagent and thereby determining the presence and/or amount of the Ab or Ag under assay.

The invention also provides a method of testing a liquid for rheumatoid factor (RF) therein, which comprises:

(a) mixing the liquid with a first microscopic or sub-microscopic particulate reagent which binds with the RF under assay;

(b) adding to the mixture from step (a) a second different microscopic or sub-microscopic particulate reagent which binds with those first reagent particles bound to RF to form an agglutinate, but which does not bind to those first reagent particles which have not bound to RF; and (c) selectively assaying the unagglutinated first or second particulate reagent and thereby determining the presence and/or amount of RF under assay.

The particulate reagents used in the method of the invention are of microscopic or sub-microscopic size, i.e. they will generally be smaller than 15 microns and most usually of the order of a few microns or submicron in size. Latex particles of such sizes are commercially available. It is known to bind Ab or Ag to microscopic particulate material such as latex. This is usually effected by providing a reactive coating on the particle, and then chemically linking or adsorbing the Ab or Ag thereon. It is also possible in certain circumstances to bind the Ab or Ag directly to the particle (with no intervening coating). Since the manner of preparation of the particulate reagents does not form part of the present invention and is well known in the art, no further description thereof will be given.

In step (c) of the method, the unagglutinated first or second particulate reagent is selectively assayed and thereby the presence and/or amount of the Ab or Ag under assay is determined. According to a highly preferred feature of the invention, the selective assay is effected by counting the free first or second particulate reagent in the presence of the agglutinate, i.e. without any separation step. This can be achieved by using first and second particulate reagents of a different size so that at least one of the two particulate reagents can be selectively counted in the reaction mixture. Counters which may be used for this purpose are known. They can be programmed to ignore all particles outside a given size range, so that by choosing appropriate sizes for the two reagents, selective counting of one in the presence of the other and of agglutinate can be achieved. Generally, the minimum particle size which can be reliably counted is about 0.6μ, so at least one of the particulate reagents will be at least this size. The other reagent may be smaller or larger. We prefer that the other reagent be smaller and, most preferably, less than 0.6μ in size so that there is no significant possibility of it interfering in the counting of the first reagent. Also, when the second reagent is smaller than the first, its reaction with the complex (formed in equilibrium (1)) is rendered more efficient. Preferably, the first reagent particles will be at least about twice the size of the second reagent particles. It is preferred that the particle size of each particulate reagent be substantially uniform.

Whilst it is a highly preferred feature of the method of the present invention to assay one of the free particulate reagents by selective counting without a separation step, it is possible to separate one (or both) of the free particulate reagents from the agglutinate and then to make the selective assay of step (c). The separation step may be effected in a variety of ways, for example by centrifugation. Preferably, there will be a difference in size between the two particulate reagents so that, upon centrifuging, the agglutinate and the larger of the two particulate reagents are sedimented, leaving the other free particulate reagent in suspension for assay. The assay may be effected by counting or in any other convenient way. For example, the remaining free particulate reagent may carry an identifying label, such as a radioactive atom, a fluorophore or an enzyme, and the assay can be effected by means of the label by known techniques.

Another way in which the separation can be very conveniently and easily achieved is by including, in one of the particulate reagents, magnetically attractable material so that, upon application of a magnetic field, that reagent (both free and in the agglutinate) may be sedimented or otherwise localised, leaving the other (non-magnetic) free reagent in suspension. Again, the free reagent may be assayed by any convenient technique such as by counting or by use of a label as described above. Magnetically attractable particles are known.

In carrying out the method of the invention to detect the presence of a particular Ab or Ag, it is merely necessary to establish whether any agglutination has occurred. That is to say, it is merely necessary to see whether any of the first or second particulate reagent has been taken up as an agglutinate. Thus for example, by counting the number of first reagent particles remaining free in the reaction mixture, and comparing the result with the number of such particles added in step (a), it can be determined whether any first reagent particles have become bound to the particular Ab or Ag under assay and thus taken up as agglutinate.

For quantitative assays, use will usually be made of standard results, i.e. results obtained using specific amounts of reagents for assaying known amounts of any particular Ab or Ag. It is then possible to determine an unknown quantity of that Ab or Ag merely by comparing the assay result of step (c) with the standard results. The use of standard results, e.g. standard curves, in this general manner is a well known technique.

The method of the invention may be used for detecting and assaying a wide variety of antibodies produced by the body against viral or bacterial infections, such as anti-DNA, anti-measles virus, anti-food antigens and anti-brucella, and other substances such as ferritin. The method of the invention is especially useful for the assay of small amounts of antibodies in human sera. For example, it is possible by the method to quantitatively assay small amounts of IgE antibodies to a particular allergen in the presence of IgE and of IgE antibodies to other antigens.

The determination and titration of IgE antibodies against certain allergens is commonly used to identify the substances to which patients are allergic. In the method of the invention, first reagent particles are coated with the allergen, e.g. extracts of house dust, cat fur, or grass pollen, by adsorption or covalent coupling, for example. This latex is then incubated in a patient's serum. If the latter contains IgE antibodies against the allergen present on the particles, the particles will take up the antibodies. By using second reagent particles carrying, for example, rabbit or goat antibodies against human IgE antibodies, it will be possible to agglutinate the allergen-coated particles provided IgE antibodies have been bound thereto. The amount of agglutination will depend on the amount of bound IgE antibodies. By using second reagent particles coated with anti-IgG or anti-IgA antibodies, it is possible to measure antibodies of other classes. To avoid interference by immunoglobulins which have not reacted with the allergen present on the particles, the latex may be centrifuged and washed. The two stages of the method may be illustrated as follows:

(1) Lx—grass pollen+IgE anti-grass pollen+IgE anti-(other allergens)→Lx—grass pollen—IgE anti-grass pollen+IgE anti-(other allergens)

(2) Lx—grass pollen—Ige anti-grass pollen+Lx-anti-IgE antibodies→agglutination

Antigen-coated latex can be replaced by antigen-coated magnetised particles. In this case, magnetic separation is used in place of centrifugal separation, and a further magnetic separation may be effected after addition of the second reagent particles, so that only the free second reagent particles remain in suspension for counting.

The method of the invention is also useful for the assay of rheumatoid factor (RF) and other similar binding proteins or agglutinators (e.g. C1q, the active fraction of mouse serum—see our U.S. Pat. No. 4,162,895, and the active fraction of mouse ascitic fluid—see our European Patent application No. 79302342.5). RF is an autoantibody directed against IgG. It can itself be an IgG, IgM or IgA class immunoglobulin. The identification of the class of RF can be useful for the diagnosis and assessment of the severity of certain diseases, and this identification can be achieved by the method of the invention. In the method, the RF is first taken up from sera by mixing the sera with, for example, rabbit IgG-coated magnetised cellulosic particles. The particles (bearing RF) are separated and washed, and then mixed with second reagent particles coated with for example goat IgG anti-human IgG (or anti-human IgA or anti-human IgM, as desired). After a magnetic separation, the free second reagent particles are counted.

The method of the invention is also useful for the assay of Ag. In this procedure, the serum containing the antigen is first mixed with latex particles having the same Ag attached thereto, and a limited quantity of Ab against the Ag. The free Ag and the latex-bound Ag compete for the Ab and the amount of Ab becoming bound to the latex-Ag (to form immune complex on the latex) will depend on the amount of free Ag in the serum sample.

The second particulate reagent is now added, which comprises as reagent Ab against the Ab used in the first stage. The second reagent thus causes agglutination of those first reagent particles which have immune complex thereon. By measuring the first or second unagglutinated reagent particles, the presence and/or amount of Ag in the serum can be determined.

This assay can, for example, be used for progesterone, using as the first particulate reagent $0.8\mu$ latex coated with ferritin-progesterone conjugate by physical adsorption, and as second particulate reagent 0.2μ particles coated by adsorption with goat IgG anti-rabbit IgG. The antiserum used is rabbit anti-progesterone antiserum.

It will be appreciated that in the method of assay for Ag described above, the assay is actually conducted on the amount of Ab available to bind with the first particulate reagent, which amount in turn is dependent on the amount of Ag present in the serum.

In the method of the invention, the first particulate reagent is selective to the analyte under assay, and preferably the first reagent particles will be larger than the second reagent particles. A large excess of the second reagent particles is used to provide for the prozone effect.

In order that the invention may be more fully understood, the following Examples are given by way of illustration only.

EXAMPLE 1

Assay of IgE antibodies in human serum

IgE antibodies to an allergen (e.g. ragweed pollen) are assayed as follows.

Latex particles of relatively large diameter (e.g. 0.79μ) are coated with the allergen, for example by simple adsorption or by covalent coupling with cyanogen bromide or hydroxylated latex. A quantity (e.g. 50 μl) of serum is mixed with a quantity (e.g. 50 μl) of a suspension of these particles in a buffer (for example $10^7$ particles/ml). The mixture is incubated for about 10 minutes at 25° C. There is then added a quantity (e.g. 50 μl) of latex particles of a relatively small diameter (e.g. 0.08μ). These particles have been coated with rabbit anti-IgE antibodies by adsorption. The particles are added to the mixture as a suspension of about $10^7$ particles/ml in a buffer.

The resulting mixture is incubated for about 10 minutes at 25° C., then diluted with about 60 ml. of GBS buffer (0.1 M glycine, 0.17 M NaCl, pH 9), and then aspirated through a particle counter arranged to ignore both large agglutinates and the latex-Ab particles. The number of unagglutinated large latex particles is inversely proportional to the amount of IgE which has bound to the allergen on the large particles and, hence, to the amount of IgE in the serum.

EXAMPLE 2

Determination of rheumatoid factor

Reagents: Rabit IgG were coupled to magnetised cellulose particles whose particle size follows a Gaussian distribution with 95% between 0.5 and 3.0 microns. Polystyrene particles of 0.8μ were coated by physical adsorption either with goat IgG anti-human IgG, goat IgG anti-human IgA, or goat IgG anti-human IgM. We previously absorbed the goat antisera by rabbit IgG to avoid cross reaction with the material coating the cellulose particles. The reaction medium consisted of a 0.1 M glycine-NaOH buffer, pH 9.2 containing 0.17 M NaCl.

A volume of 75 μl of the suspension of magnetic particles (5 mg/ml glycine buffer) was incubated in 3 ml-glass tube with 300 μl of various dilutions of serum for 45 minutes at room temperature on a vortex mixer. The magnetic particles were then washed 3-times with 2 ml of glycine buffer using a magnet to trap the particles. After the last wash and addition of 75 μl glycine buffer, the suspension was distributed into three glass tubes, each one being used for the determination of one class of antibodies. A sample of 100 μl of the suspension (0.625 g/l) of anti-IgG latex was added to tube No. 1, of anti-IgA latex to tube No. 2, and of anti-IgM latex to tube No. 3. Latex and cellulose particles were incubated for 30 minutes at room temperature on a vortex mixer. After dilution with 2 ml glycine buffer, the tubes were reversed twice and the magnetic particles retained on the tube wall with a magnet. A volume of 250 μl of the supernatant was diluted in 2 ml glycine buffer and aspirated in a Technicon AutoAnalyser. The particles which were not retained by the magnetised particles were counted in the AutoCounter. The number of particles was related to the dilution titre of tested serum.

The method of the invention may be operated in a discrete or in a continuous flow automated manner. As an example of an automated system, 50 μl of prepared sample are aspirated by a peristaltic pump simultaneously with 50 μl of latex-allergen. The resulting stream passes for 10 minutes through a vibrating mixing coil (50 hz). On emerging from the coil, the stream joins another stream flowing at 0.1 ml/minute containing latex-Ab conjugate. The combined streams pass through a second vibrating mixing coil for a further 5 minutes. The stream is diluted 400-fold and then passes through the cell counter equipped with double threshold to eliminate both agglutinated particles and the small latex-Ab.

It will be understood that the Examples described above are for the purposes of illustration only and are not limitative. It is further to be understood that, in the event that the serum or other liquid under test contains substances which might interfere with the method of the invention, the serum or liquid is treated to remove or inactivate such substances.

We claim:

1. A method of testing a liquid for an Ab or Ag therein, which comprises:
   (a) mixing the liquid with a first microscopic or sub-microscopic particulate reagent which binds with the Ab or Ag under assay to form a complex therewith;
   (b) adding to the mixture from step (a) a second different microscopic or sub-microscopic particulate reagent which binds with the complex formed in step (a) to form an agglutinate, but does not bind with free first particulate reagent; and
   (c) selectively assaying the unagglutinated first or second particulate reagent and thereby determining the presence and/or amount of the Ab or Ag under assay.

2. A method according to claim 1, wherein the first and second particulate reagents are of a different size such that, in step (c), at least either the unagglutinated first or second reagent particles can be selectively counted in an admixture of first and second reagent particles and the agglutinate, without any separation step, and wherein the step (c), the unagglutinated first or second particulate reagent is assayed by such selective counting.

3. A method according to claim 2, wherein one of said particulate reagents has a particle size less than 0.6 microns, and the other has a particle size greater than 0.6 microns.

4. A method according to claim 1, wherein the second particulate reagent is smaller than the first particulate reagent.

5. A method according to claim 1, wherein the step (c) at least one of the free first and second particulate reagents is separated from the agglutinate prior to the selective assay.

6. A method according to claim 5, wherein the separation is effected by centrifuging.

7. A method according to claim 5, wherein one of the first and second particulate reagents includes magnetically attractable material, and the separation is effected by applying a magnetic field to separate the agglutinate and free magnetic particles of one reagent from the free particles of the other reagent.

8. A method according to claim 5, wherein one of the particulate reagents carries a label, and the free particles thereof after separation from the agglutinate are assayed by their label.

9. A method according to claim 5, wherein the or one of the free particulate reagents which has been separated from the agglutinate is assayed by counting.

10. A method of testing a liquid for rheumatoid factor (RF) therein, which comprises
(a) mixing the liquid with a first microscopic or sub-microscopic particulate reagent which binds with the RF under assay;
(b) adding to the mixture from step (a) a second different microscopic or sub-microscopic particulate reagent which binds with those first reagent particles bound to RF to form an agglutinate, but which does not bind to those first reagent particles which have not bound to RF; and
(c) selectively assaying the unagglutinated first or second particulate reagent and thereby determining the presence and/or amount of RF under assay.

11. A method according to claim 10, wherein in step (b) the second reagent is an IgG, IgM or IgA whereby, in step (c) the IgG, IgM or IgA, fraction respectively, of the RF is determined.

12. A method according to claim 1, wherein the particulate reagents each comprise latex particles carrying a reagent.

13. A method according to claim 10 wherein the particulate reagents each comprise latex particles carrying a reagent.

14. A method according to claim 1 wherein the amount of an Ab in a liquid is assayed, and wherein the amount of said Ab is dependent on the amount of an Ag also present in the liquid whereby, from the result of the assay, the amount of Ag can be determined.

15. A method according to claim 1 which is effected by continuous flow techniques.

* * * * *